United States Patent [19] [11] 3,956,328
Irikura [45] May 11, 1976

[54] S-TRIAZOLO(1,5-A)PYRIDINE DERIVATIVE
[75] Inventor: Tsutomu Irikura, Oizumigakuen, Japan
[73] Assignee: Kyorin Seiyaku Kabushiki Kaisha, Tokyo, Japan
[22] Filed: Sept. 4, 1974
[21] Appl. No.: 503,089

[30] Foreign Application Priority Data
Oct. 30, 1973 Japan.............................. 48-121975

[52] U.S. Cl...................... 260/268 BC; 260/296 H; 424/250
[51] Int. Cl.². ........................................ C07D 401/14
[58] Field of Search.............................. 260/268 BC

[56] References Cited
UNITED STATES PATENTS
3,381,009  4/1968  Palazzo et al................. 260/268 BC
3,472,853  10/1969  Archer.......................... 260/268 BC Primary Examiner—Paul M. Coughlan, Jr.
Attorney, Agent, or Firm—Toren, McGeady and Stanger

[57] ABSTRACT

A compound of the formula (I),

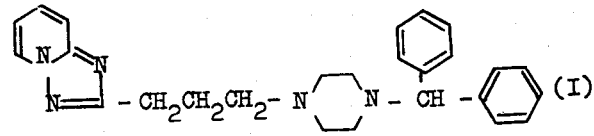

and the non-toxic acid addition salts thereof are disclosed. These compounds and salts are useful as therapeutic agents for allergic diseases.

3 Claims, No Drawings

S-TRIAZOLO(1,5-A)PYRIDINE DERIVATIVE

DETAILED DESCRIPTION OF THE INVENTION

This invention relates to a novel chemical compound, 2-[3-(4-diphenylmethyl-1-piperazinyl)propyl]-s-triazolo[1,5-a]pyridine, of value as a therapeutic agent for allergic diseases, especially for allergic asthma.

The new compound of the present invention is represented by the following formula (1)

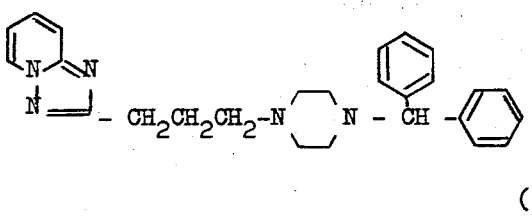

(1)

and includes not only the base conforming to this formula but also the corresponding non-toxic acid addition salts, such, for example, the dihydrochloride formed between the base and hydrogen chloride.

As the result of the studies on the preparation and physiological properties of various triazolo[1,5-a]pyridine derivatives, it has been found that the compound of the present invention possesses interesting pharmacodynamic properties and particularly is a very useful therapeutic agent for allergic asthma.

The compound in the present invention may be prepared by the reaction of the compound of the formula

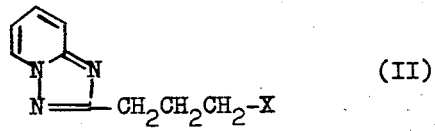

(II)

in which X represents the residue of a reactive ester (e.g. a halogen atom or arylsulfonic ester radical, such as the p-toluene sulfonate radical), with N-diphenylmethylpiperazine of the formula (III).

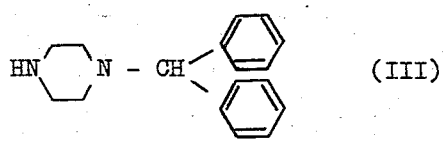

(III)

The reaction is preferably effected by heating a substantially equimolar mixture of the reactants in an appropriate organic solvent, such as, for example, dimethylformamide, toluene, xylene, 1,2-diethoxyethane, and so on, in the presence of an equimolar or a slightly excess deacidifying agent, such as, for example, potassium carbonate, triethylamine, and so on, at a temperature of the boiling point of the solvent employed. When the compound (II) in which X is a chlorine radical is used, it is generally prefered to add a catalytic amount of an alkali iodide, such as, sodium iodide or potassium iodide, in order to obtain in a higher yield.

The physiological properties of the compound of the present invention are roughly as follows.

Acute toxicity:

The acute oral $LD_{50}$ of the present compound is 625 mg/kg (confidence limit 507–768 mg/kg) for male ddN mice and 485 mg/kg (confidence limit 418–563 mg/kg) for female ddN mice.

That of homochlorcyclyzine used as a standard drug is reported to be 353 mg/kg for mice. The acute oral $LD_{50}$ of the present compound is 1,370 mg/kg (confidence limit 1,051-1,790 mg/kg) for male wistar rats and below 450 mg/kg for female wistar rats. The present compound shows a lower toxicity than that of homochlorcyclizine.

The inhibitory actions of the present compound on the experimentally allergic asthma attack in guinea pigs:

The present compound is studied on asthma attacks induced by the antigen-antibody reaction in guinea pigs. The guinea pigs are sensitized passively by the injection of 0.1 to 0.3 ml/100g body weight of rabbit antiserum to BSA (bovine serum albumin) into the ear vein. Forty six hours after passive sensitization, the guinea pigs are orally given the tested compounds. Two hours after oral administration, the asthma attack is provoked by an aerosol injection (0.1 ml/min.) of 1% BSA solution in physiological saline into the plastic chamber in which the testing guinea pig is placed. The symptoms of the asthma attack are observed for 10 minutes and scored on the following shock indices. The shock indices are examined by the shock grades, No. of collapsed guinea pigs/No. of used animals and survival rate.

| The shock grades are as follows: | |
|---|---|
| 0 | no changes |
| 1 | slight stimulation of expiration |
| 2 | stimulation of expiration (labored expiration) or slight singultation |
| 3 | attack of singultation |
| 4 | the strongest attack of collapse and struggle but recovery from collapse within 5 minutes |
| 5 | recovery from collapse within 5 to 10 minutes |
| 6 | interruption of expiration to death within 10 minutes |

Tables 1 and 2 show the effects of the present compound. An oral 1 mg/kg dose of the present compound inhibits shock death and more than oral 5 mg/kg dose completely inhibits collapse.

On the incidences of asthma attack, more than 0.5 mg/kg dose inhibits significantly comparing with that of non treated guinea pigs, and a 5 mg/kg dose suppresses completely severe asthma attack. The present compound prohibits the asthma attack more significantly than that of homochlorocyclizine.

Table 1

Effects of the present compound and homochlorcyclizine on BSA induced asthma in guinea pigs

| Amount of rabbit antiserum to BSA ml/100 g | Tested compounds | Dose mg/kg p.o. | A/B | | Survival rate | |
|---|---|---|---|---|---|---|
| | * | 0 | 16/16 | (100) | 7/16 | (43.7) |
| | | 0.5 | 3/6 | (50) | 5/6 | (83.3) |
| | ** | 1.0 | 4/10 | (40) | 10/10 | (100) |
| 0.1 | | 5.0 | 0/6 | (0) | 6/6 | (100) |
| | | 0.5 | 4/6 | (66.7) | 5/6 | (83.3) |
| | homochlor. | 1.0 | 6/10 | (60) | 10/10 | (100) |
| | | 5.0 | 1/6 | (16.7) | 6/6 | (100) |
| | * | 0 | 16/16 | (100) | 2/16 | (12.5) |

Inhibitory actions on histamine-induced asthma attack: Male guinea pigs, of about 300 g body weight are used. Asthma attack is provoked by an aerosol of 0.2% histamine dihydrochloride solution in physiological saline for 10 minutes. The inhibitory actions are examined by shock grades, No. of collapsed guinea pigs/No. of provoked guinea pigs and survival rate. The tested compounds are orally given 2 hrs. prior to spraying of histamine solution.

Table 3 shows severity of asthma attack, No. of collapsed guinea pigs/No. of provoked guinea pigs, and survival rate. The present compound markedly and significantly inhibits asthma attack as compared to non treatment and homochlorcyclizine did.

Table 1-continued

Effects of the present compound and homochlorcyclizine on BSA induced asthma in guinea pigs

| Amount of rabbit antiserum to BSA ml/100 g | Tested compounds | Dose mg/kg p.o. | A/B | | Survival rate | |
|---|---|---|---|---|---|---|
| 0.2 | ** | 5 | 0/6 | ( 0 ) | 6/6 | (100) |
|  | homochlor. | 5 | 4/6 | (66.7) | 6/6 | (100) |
|  | * | 0 | 10/10 | (100) | 2/10 | ( 20) |
| 0.3 | ** | 5 | 0/5 | ( 0 ) | 5/5 | (100) |
|  | homochlor. | 5 | 1.5 | ( 20) | 5/5 | (100) |

*non treatment **the present compound
homochlor.: homochlorcyclizine
A/B : No. of collapsed guinea pigs/No.of provoked guinea pigs
( ): percentage Table 2

Inhibitory action of the present compound and homochlorcyclizine on BSA-induced asthma in guinea pigs

| Amount of rabbit antiserum to BSA ml/100g | Tested compounds | Dose mg/kg p.o. | Severity of asthma attack 0 1 2 3 4 5 6 | Statistical significance* | |
|---|---|---|---|---|---|
|  | non treatment | 0 | 0 0 0 0 3 4 9 | | |
|  | the present compound | 0.5 | 0 0 1 2 2 0 1 | $z_1$=2.618 | p<0.01 |
|  |  | 1.0 | 0 2 2 2 4 0 0 | $z_1$=4.032 | p<0.0001 |
|  |  | 5.0 | 0 2 3 1 0 0 0 | $z_1$=3.686 | p<0.001 |
| 0.1 |  | 0.5 | 0 0 2 0 2 1 1 | $z_1$=2.235 | p<0.02 |
|  | homochlor. | 1.0 | 0 1 2 1 5 0 1 | $z_1$=3.368 | p<0.001 |
|  |  | 5.0 | 0 1 1 3 0 1 0 | $z_1$=3.576 | p<0.001 |
|  | non treatment | 0 | 0 0 0 0 1 1 4 | | |
|  | the present |  |  | $z_1$=4.112 | p<0.0001 |
| 0.2 | compound | 5 | 0 1 2 3 0 0 0 |  |  |
|  |  |  |  | $z_2$=2.067 | p<0.04** |
|  | homochlor. | 5 | 0 0 1 1 3 1 0 | $z_1$=3.993 | p<0.0001 |
|  | non treatment | 0 | 0 0 0 0 2 0 8 | | |
| 0.3 | the present | 5 | 0 1 2 2 0 0 0 | $z_1$=3.26 | p<0.001 |
|  | compound |  |  | $z_2$=2.008 | p<0.05** |
|  | homochlor. | 5 | 0 0 0 4 1 0 0 | $z_1$=3.23 | p<0.002 |

*Statistical comparisons were carried out with the Mann and Whitneys' U test.
$z_1$: The statistical value between non treatment and each tested compound.
$z_2$: The statistical value between the present compound and homochlorcyclizine.
**The results show that the present compound has a more significant inhibitory action on BSA-induced asthma attack than that of homochlorcyclizine.

Table 3

Inhibitory actions of the present compound and homochlorcyclizine on histamine-induced asthma attack

| Treatment | Dose mg/kg p.o. | Severity of asthma attack 0 1 2 3 4 5 6 | A/B | | Survival rate | |
|---|---|---|---|---|---|---|
| non treatment 1 | 0 | 0 0 0 0 0 0 20 | 20/20 | (100) | 0/20 | ( 0 ) |
| non treatment 2 | 0 | 0 0 0 0 0 0 7 | 7/7 | (100) | 0/7 | ( 0 ) |
| the present compound | 0.156 | 0 0 0 0 0 0 10 | 10/10 | (100) | 0/10 | ( 0 ) |
|  | 0.313 | 0 0 0 0 5 5 0 | 10/10 | (100) | 10/10 | (100) |
|  | $z_1$>5 markedly significant difference from non treatment 1 | | | | | |
|  | 0.625 | 0 0 0 1 8 1 0 | 9/10 | ( 90) | 10/10 | (100) |
|  | $z_1$>5 markedly significant difference from non treatment 1 | | | | | |
|  | 1.25 | 0 0 1 5 4 0 0 | 4/10 | ( 40) | 10/10 | (100) |
|  | $z_1$>5 markedly significant difference from non treatment 1 | | | | | |
|  | 2.50 | 2 0 3 5 1 0 0 | 1/11 | (9.1) | 11/11 | (100) |
|  | $z_1$>5 markedly significant difference from non treatment 1 | | | | | |
|  | $z_2$=2.332 significant difference from homochlorcyclizine (250 mg/kg)(p<0.02) | | | | | |
|  | 10.0 | 4 0 2 0 0 0 0 | 0/6 | ( 0 ) | 6/6 | (100) |
|  | $z_1$=3.321 significant difference from non treatment 2 (p<0.0005) | | | | | |
|  | $z_2$=2.844 significant difference from non treatment 1 (p<0.005) | | | | | |
| homochlor. | 2.50 | 0 0 1 5 4 1 0 | 5/11 | (45.5) | 11/11 | (100) |
|  | $z_1$>5 markedly significant difference from non treatment 2 | | | | | |
|  | 10.0 | 0 0 1 4 1 0 0 | 1/6 | (16.7) | 6/6 | (100) |

Table 3-continued

Inhibitory actions of the present compound and
homochlorcyclizine on histamine-induced asthma attack

| Treatment | Dose mg/kg p.o. | Severity of asthma attack 0 1 2 3 4 5 6 | A/B | Survival rate |
|---|---|---|---|---|

$z_1=3.315$ significant difference from non treatment 1 (p 0.0005)

A/B: No. of collapsed guinea pigs/ No. of provoked guinea pigs. Statistical comparisons were carried out with the Mann and Whtineys' U test.

Anti histaminic action of the present compound on guinea pig tracheal chain strip:

On the histamine-induced contraction of guinea pig tracheal chain strips, the inhibitory rate of the present compound is 124% ($4\times10^{-5}$M of the present compound was suspended in Tyrodes solution), and that of homochlorcyclizine ($4\times10^{-5}$M) is 74%.

Anti cholinergic action:

The present compound is not found to have anti acetylcholinergic action. The inhibitory action of the present compound on passive cutaneous anaphylaxis (PCA) reaction:

1. heterologous PCA in guinea pigs

Male guinea pigs are passively sensitized by the intradermal injection of rabbit antiserum to egg albumin and challenged by the intravenous injection of egg albumin 4 hrs. after the sensitization. The test compounds are orally given 30 min. before the challenge. The extravasation of blue dye at injected skin is extracted with formamide and optically determined as shown in Table 4, the inhibitory rate of the blue dye extravasation of the present compound (25 mg/kg po) is 57.8%, and that of homochlorcyclizine (25 mg/kg po) is 41.7%.

2. homologous PCA in rats

Male wistar or SD rats are passively sensitized by Motas method (Immunology 7, 681, 1964) and challenged by the intravenous injection of wistar or SD rat antiserum to egg albumin or horse serum. The inhibitory action of the present compound on homologous PCA (induced by reaginlike, mast cell sensitizing antibody) is shown in Table 5.

Table 4

Effects of the present compound and homochlorcyclizine on heterologous passive cutaneous anaphyloxis reaction (induced by the intradermally injection of rabbit antiserum to egg albumin) in guinea pigs

| Drug | Dose mg/kg po | Administration before challenge | Inhibition % of extravasation of blue dye |
|---|---|---|---|
| non treatment | 0 | 0 | 0 |
| the present compound | 25 | 30 min. | 57.8 |
| homochlor. | 25 | 30 min. | 41.7 |

Table 5

Effects of the present compound on homologous passive cutaneous reaction (induced by rat antiserum to egg albumin or horse albumin) in rats

| Drug | Dose mg/kg po | Rat strain | | after sensiti. | before challenge | Inhibit. % |
|---|---|---|---|---|---|---|
| non treatment | 0 | Wistar | egg albu. | 72 hrs. | 0 min. | 0 |
| the present compound | 25 | " | " | " | 30 | 64.3 |
|  | 50 | " | " | " | 30 | 88.8 |
| non treatment | 0 | SD | horse serum | 48 | 0 | 0 |
| the present compound | 100 | " | " | " | 3 hrs. | 94.8 | after sensiti.: challenge after sensitization
before challenge: administration before challenge
Inhibit. %: Inhibition % of extravasation of blue dye
egg.albu.: egg albumin Table 6

Effect of the present compound on Schultz-Dale reaction in guinea pig ileum sensitized actively with egg albumin

| Antigen | Drug | Concentration | Inhibition % |
|---|---|---|---|
| egg albumin | the present compound HCl salt | $2\times10^{-7}$M | 32.2 |
|  |  | $3\times10^{-7}$M | 55.6 |
|  |  | $5\times10^{-7}$M | 60.1 |

When 25 mg/kg and 50 mg/kg dose of the present compound are orally administered 30 min. before challenge, the inhibitory rates in Wistar strain rats are 64.3% and 88.8% respectively.

The inhibitory rate in SD strain rats is 94% in 100 mg/kg dose of the present compound 3 hrs. before challenge.

The present compound markedly inhibits reaginlike, mast cell sensitizing antibody-induced PCA in either Wistar or SD rat. The inhibitory action of the present compound on Schultz-Dale reaction in guinea pigs:

Male guinea pigs are actively sensitized and their ileum preparations are treated by Schultz-Dales method (J. Pharmacol. Exp. Ther., 4, 167, 1913). The inhibitory rates are 32.2, 55.6 and 60.1% respectively at the concentrations of $2\times$, $3\times$ and $5\times10^{-7}$M of the present compound. The present compound markedly inhibits Schultz-Dale reaction in actively-sensitized guinea pig ileum. These preceeding pharmacological properties of the present compound are due to triazolo [1,5-a]pyridine.

For purposes of illustration only, this invention will now be illustrated by the following examples. Of course, this invention shall not be limited to the following examples. Firstly, the preparation of the starting material having the formula II is described for the purpose of reference, because the compound is also a novel one.

EXAMPLE FOR REFERENCE

Preparation of 2-(3-chlorpropyl)-s-triazolo 1,5-a pyridine.

a. Preparation of 2-(3-hydroxypropyl)-s-triazolo 1,5-a-pyridine.

A stirred suspension of 105 g of 1,2-diaminopyridinium iodide, 61 g of anhydrous potassium carbonate, and 76 g of γ-butyrolactone in 1,2-diethoxyethane is refluxed for 8 hrs. After cooling, the mixture is concentrated under a reduced pressure. To the residue 1,000 ml of water is added and the mixture is stireed for a period of time. Then 1,000 ml of chloroform is added to the mixture under continuous stirring. The cystalline product that is separated is collected by filtration. It weighs 30 g. The chloroform layer of the filtrate is separated from the water layer, dried over anhydrous sodium sulfate, and concentrated to give a viscous oil, which solidifies by trituration with petroleum ether. The crystalline product weighs 74 g. The total crystalline product (104g) is recrystallized from ethyl acetate to give 87g of colorless prisms, melting point 71.5°–73°C.

| | | C | H | N |
|---|---|---|---|---|
| Anal. Calcd. | for $C_9H_{11}ON_3$: | 61.00 | 6.26 | 23.72 |
| Found: | | 60.82 | 6.14 | 23.48 | b. To a solution of 34.5g of 2-(3-hydroxypropyl)-s-triazolo-[1,5-a]pyridine in 500 ml of chloroform is added dropwise 77g of phosphorous oxychloride at a temperature of from 5° to 15°C. After the addition is completed, the reaction mixture is heated on a water bath for 1 hr. and then added to 300 g of ice-water. The mixture is then treated with an aqueous sodium hydroxide solution. Then the organic layer is separated from the aqueous layer, dried over anhydrous sodium sulfate and concentrated to give the residue, which is chromatographed over alumina with benzene. Twenty-three grams of 2-(3-chloropropyl)-s-triazolo[1,5-a]pyridine are obtained as colorless needles after recrystallization from cyclohexane, melting point 56.5°–57°C.

| | | C | H | N |
|---|---|---|---|---|
| Anal. Calcd. | for $C_9H_{10}N_3Cl$: | 55.25 | 5.15 | 21.48 |
| Found: | | 55.58 | 5.33 | 21.55 |

EXAMPLE 1

A mixture of 2.0 g of 2-(3-chloropropyl)-s-triazolo[1,5-a]pyridine, 2.5 g of N-diphenylmethylpiperazine, 1.4 g of anhydrous potassium carbonate, and 0.5 g of sodium iodide in 70 ml of dimethylformamide is refluxed for 5 hrs. The reaction mixture is cooled and the precipitate is filtered off. The filtrate is concentrated under a reduced pressure and to the residue, 60 ml of chloroform is added. The resulting chloroform solution is extracted three times with 90 ml of a normal solution of hydrochloric acid. The combined acidic layer is washed twice with chloroform, and treated with potassium carbonate. The basic mixture is extracted with chloroform and the extract is dried over anhydrous sodium sulfate and concentrated to give a crude product, which is chromatographed over silicagel with ethyl acetate, followed with ethyl acetate containing methanol (10%). Two grams of 2-[3-(4-diphenylmethyl-1-piperazinyl)propyl]-s-triaxolo[1,5-a]pyridine of a melting point of 92°–94°C are obtained from the fraction of ethyl acetate-methanol solution. Recrystallization from benzenecyclohexane yields 1 g (24%) of colorless prisms, melting point 105.5°C.

| | | C | H | N |
|---|---|---|---|---|
| Anal. Calcd. | for $C_{26}H_{29}N_5$: | 75.88 | 7.10 | 17.02 |
| Found: | | 75.63 | 7.26 | 17.00 |

To obtain the dihydrochloride salt, a solution of ethanol containing hydrogen chloride is added to a solution of the above free base in ethanol. This mixture is concentrated under a reduced pressure to give a crystalline residue, which is recrystallized from ethanol-petroleum ether to hydroscopic colorless fine needles, melting point 179°–180°C.

| | | C | H | N |
|---|---|---|---|---|
| Anal. Calcd. | for $C_{26}H_{29}N_5.2HCl.3H_2O$: | 57.98 | 6.92 | 13.00 |
| Found: | | 57.90 | 6.77 | 13.10 |

The salt is soluble in water and in alcohols. The structural formula is:

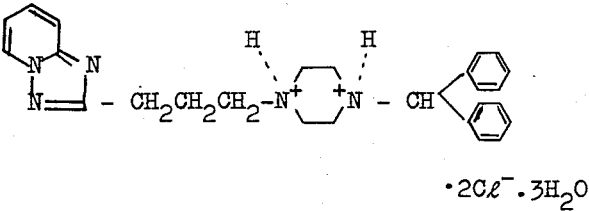

What is claimed is:
1. A compound of the formula (I),

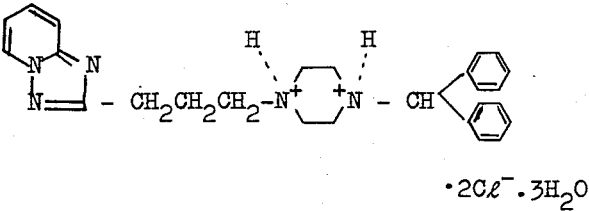

(I)

or non-toxic acid addition salts thereof.

2. 2-[3-(4-diphenylmethyl-1-piperazinyl)-propyl]-s-triazolo[1,5-a]pyridine or non-toxic acid addition salts thereof.

3. the dihydrochloride salt of 2-[3-(4-diphenylmethyl-1-piperazinyl)propyl]-s-triazolo[1,5-a]pyridine.

* * * * *